(12) United States Patent
Moreau et al.

(10) Patent No.: US 6,177,415 B1
(45) Date of Patent: Jan. 23, 2001

(54) BACTERIOHOPANETETROL AND RELATED COMPOUNDS USEFUL FOR MODULATION OF LIPOXYGENASE ACTIVITY AND ANTI-INFLAMMATORY APPLICATIONS

(75) Inventors: Robert A. Moreau, Quakertown; Kevin B. Hicks, Malvern, both of PA (US)

(73) Assignee: The United States of America as represented by the Secretary of Agriculture, Washington, DC (US)

( * ) Notice: Under 35 U.S.C. 154(b), the term of this patent shall be extended for 0 days.

(21) Appl. No.: 08/844,631

(22) Filed: Apr. 21, 1997

(51) Int. Cl.[7] .............. A61K 31/56; A61K 31/58
(52) U.S. Cl. .............. 514/171; 514/172; 514/182; 514/729; 514/738; 514/766
(58) Field of Search .................. 514/724, 729, 514/738, 171, 172, 182, 766

(56) References Cited

U.S. PATENT DOCUMENTS

| | | | |
|---|---|---|---|
| 3,665,012 | * | 5/1972 | Bretschneider et al. ......... 260/326.3 |
| 5,086,076 | * | 2/1992 | Herman ........................ 514/724 |
| 5,260,342 | * | 11/1993 | Herman ........................ 514/724 |
| 5,364,879 | * | 11/1994 | Herman ........................ 514/452 |

FOREIGN PATENT DOCUMENTS

| | | | |
|---|---|---|---|
| 2-73012 | * | 3/1990 | (JP) . |
| 4-290846 | * | 10/1992 | (JP) . |
| 5-117142 | * | 5/1993 | (JP) . |

OTHER PUBLICATIONS

CAPLUS: 412743, 1987.*
CAPLUS:741725, 1995.*
CAPLUS 1997:273931.*
Parthasarathy et al., *Prog. Lipid Res.*, vol. 31, No. 2, p. 127–143 (1992).
Nagumo et al., *Toxicology Letters*, vol. 58, p. 309–313 (1991).
Chen et al., *Biol. Pharm. Bull.*, vol. 18(3), p. 421–423 (1995).
Roth et al., *Analytical Biochemistry*, vol. 224, p. 302–308 (1995).
Moreau et al., *Analytical Biochemistry*, vol. 224, p. 293–301 (1995).
Safayhi, H., et al. "Anti–Inflammatory Actions of Pentacyclic Triterpenes", *Planta Med.*, vol. 63, pp. 487–493, 1997.

* cited by examiner

*Primary Examiner*—Shean C. Wu
(74) *Attorney, Agent, or Firm*—M. Howard Silverstein; John D. Fado; Jaenelle S. Graeter

(57) ABSTRACT

The arachidonic acid-metabolizing hopanoid tetrahydroxybacteriohopane (THBH) was isolated from *Zymomonas mobilis* and was found to inhibit soybean 15-lipoxygenase, and thus lipoxin biosynthesis, with an $IC_{50}$ of about 10 $\mu$M. The activities of two other arachidonic acid-metabolizing enzymes, human 5-lipoxygenase (involved in prostaglandin biosynthesis) and prostaglandin H synthase, were unaffected by THBH. Subsequent studies showed that THBH was effective as an anti-inflammatory agent in topical applications.

7 Claims, 4 Drawing Sheets

BACTERIOHOPANETETROL AND RELATED COMPOUNDS USEFUL FOR MODULATION OF LIPOXYGENASE ACTIVITY AND ANTI-INFLAMMATORY APPLICATIONS

BACKGROUND OF THE INVENTION

1. Field of the Invention

All of the nonsteroidal anti-inflammatory drugs in current use inhibit both 5-lipoxygenase activity and 15-lipoxygenase activity. These enzymes are involved in prostaglandin biosynthesis and in lipoxin biosynthesis, respectively. Thus, these drugs effect a broad range of activities. In addition, most have side-effects related to irritation of the stomach. This invention relates to compounds which inhibit only the lipoxin biosynthetic pathway. This degree of specificity is very useful in treating atherosclerosis and asthma since the etiology of both pathological conditions involve a 15-lipoxygenase.

2. Description of the Related Art

Hopanoids are lipids which are pentacyclic triterpene derivatives of hopane. The compounds are cyclic and branched and are therefore generally considered very stable. They have been found preserved in the organic matter of sedimentary material with only small structural changes. They have thus been successfully utilized as biomarkers in geological sediments (Ourisson et al. 1984. *Annu. Rev. Microbiol.* vol 47, pp. 301–333; Ourisson et al. 1979. *Pure Appl. Chem.* vol. 51, pp. 709–729).

Hopanoids are also found in numerous species of bacteria and cyanobacteria (Rohmer et al. 1984. *J. Gen. Microbiol.* vol. 130, pp. 1137–1150), some species of fungi (Tsuda and Isobe. 1965. *Tetrahedron Lett.* vol. 27, pp. 709–729; van Eijk et al. 1986. *Tetrahedron Lett.* vol. 27, pp. 2522–2534), lichens (Ejiri and Shibata. 1974. *Phytochemistry.* vol. 13, p. 2871) and a few species of higher plants (Ourisson et al. 1979, supra). They are localized in bacterial membranes and, since they possess some structural similarity to sterols which are known membrane stabilizers in eukaryotes (Ourisson et al. 1984, supra), they have been implicated in both prokaryotic and eukaryotic membrane stabilization.

In addition, some hopanoids have been reported to show anti-tumor cell effects. Nagumo et al. (1991. *Toxicol. Lett.* vol. 58, pp. 309–313) tested the cytotoxicity of a hopanoid isolated from *Rhodopseudomonas palustris* against mouse leukemia cells, and Chen et al. (1995. *Biol. Pharm. Bull.*, vol. 18, no. 3, pp. 421–423) investigated cytotoxic effects of a number of hopanoids isolated from *Acetobacter aceti,* also against mouse leukemia cells.

Heretofore, there have been no reports or suggestions of anti-inflammatory activity exhibited by hopanoid compounds.

SUMMARY OF THE INVENTION

We have discovered that naturally-occurring hopanoids possess unique properties in that they block only one biochemical pathway, i.e. that of lipoxin biosynthesis.

In accordance with this discovery, it is an object of the invention to provide a composition comprising hopanoids effective for blocking lipoxygenases and lipoxin biosynthesis thus serving as an effective anti-inflammatory agent.

Other objects and advantages will become readily apparent from the following description.

DETAILED DESCRIPTION OF THE INVENTION

Figure 1A:
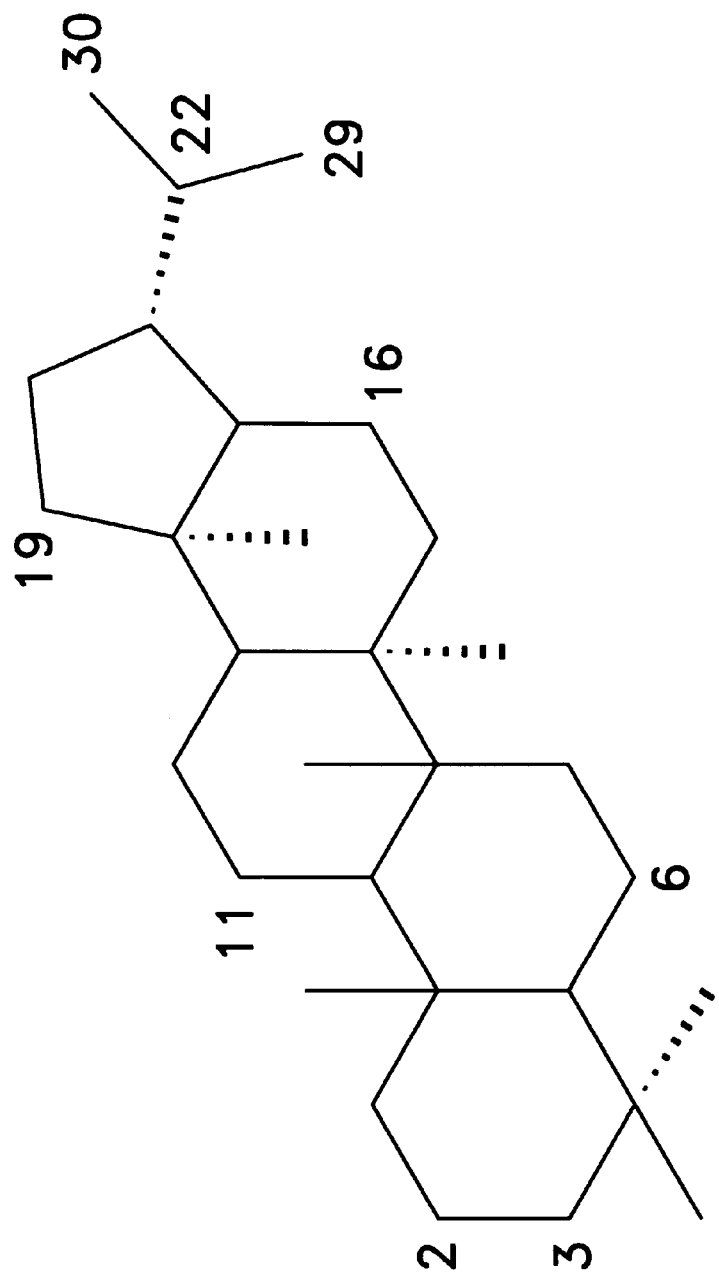
FIG. 1 shows the structures of hopane (a) and the three natural hopanoids tetrahydroxybacteriohopane, THBH (b), tetrahydroxybacteriohopane glucosamine, THBH-GA (c) and tetrahydroxybacteriohopane ether, THBH-Et (d).
Figure 1B:
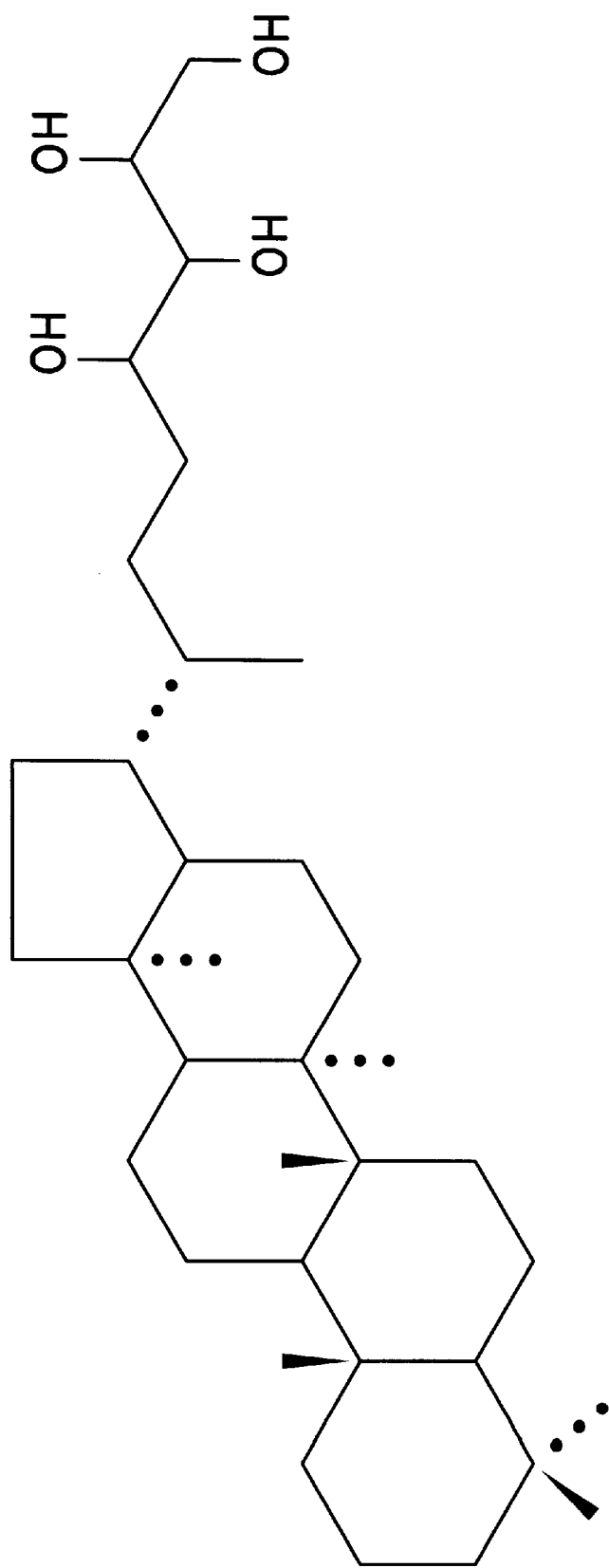
Figure 1C:
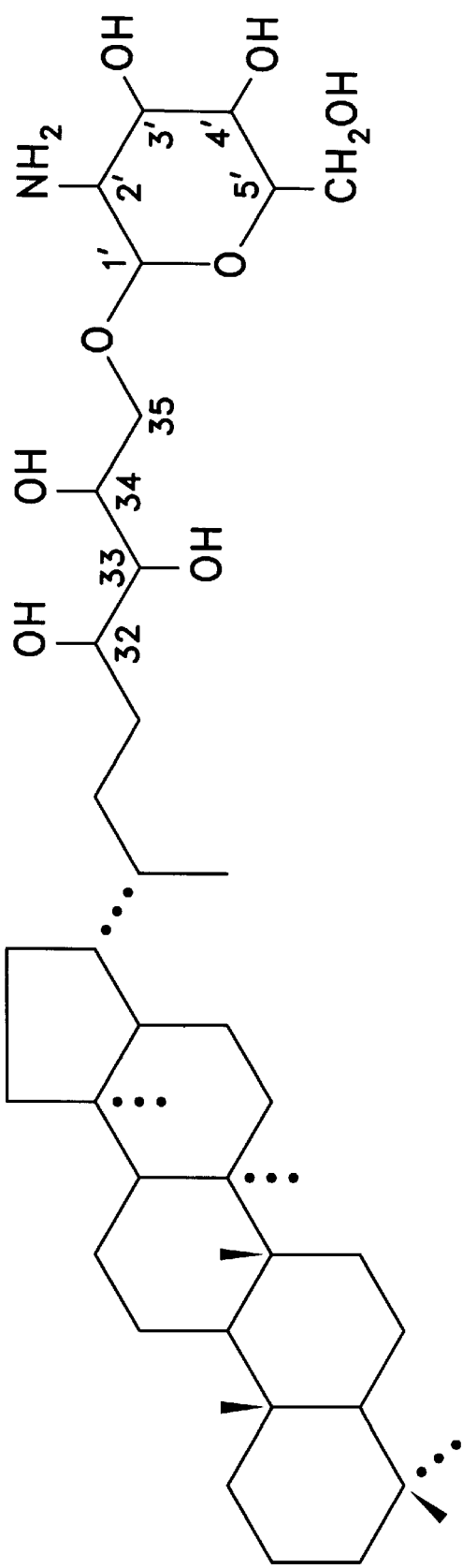
Figure 1D:
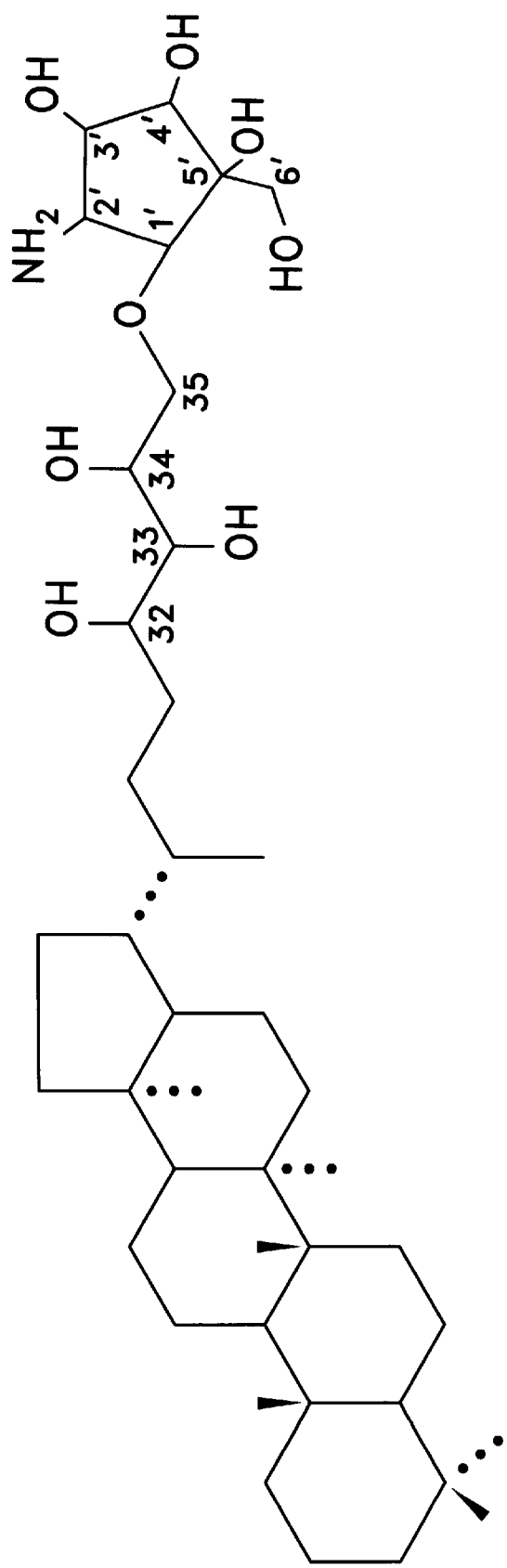

Hopanoids are naturally-occurring lipid compounds which are derivatives of hopane (FIG. 1a). They are pentacyclic triterpenes and are found in the membranes of prokaryotes, such as bacteria and blue-green algae. They are similar in size and shape to sterols such as cholesterol.

Hopanoids may be obtained by extraction from prokaryotic preparations which have been grown under either aerobic or anaeronbic conditions. For example, they may be isolated from *Zymomonas mobilis* (*Z. mobilis*), an ethanol-producing bacterium reported to contain five hopanoids (Schulenberg-Schell et al. 1989. *Anal. Biochem.* vol. 181, pp. 120–124). The compounds may be isolated by any method known in the art to be effective for that purpose. Exemplary methods are described by Moreau et al. (1995. *Anal. Biochem.* vol. 224, pp. 293–301) and Roth et al. (1995. *Anal. Biochem.* vol. 224, pp. 302–308, both references herein incorporated by reference). Essentially, both aerobic and anaerobic fermentation methods are described wherein strains of *Z. mobilis* were maintained on a solid medium [2% glucose, 1% yeast extract (Difco Laboratories, Detroit, Mich.), and 1.5% agar (Difco Laboratories, Detroit, Mich.)] at 28° C. and subcultured weekly (all media compositions are reported as w/v). The bacterium was grown in liquid medium consisting of 2% glucose, 1% yeast extract, 0.2% $KH_2PO_4$, pH 6.0 (1 liter media in 2.8-liter Fernbach flasks). Starter cultures (20 ml of liquid medium in a 100-ml flask) were inoculated with a turbid cell suspension (approximately 1 ml) prepared from cells grown overnight on the above solid medium at 28° C. Starter culture flasks were incubated overnight at 28° C. with shaking (250 rpm), and one 20-ml starter culture was used to inoculate each 1-liter flask. The 1-liter cultures were incubated at 28° C. with shaking (250 rpm) for 1 to 3 days.

Anaerobic cultures were grown in a 70-liter pilot plant fermentor (ABEC, Inc., Allentown, Pa.) at 28° C. under nitrogen sparging. The medium (40-liter total volume) consisted of 10% glucose, 0.5% yeast extract, 0.1% $(NH_4)_2SO_4$, 0.1% $KH_2PO_4$, and 0.05% $MgSO_4\text{-}7H_2O$; pH was controlled at approximately 5.0 by periodic additions of 0.5 M KOH. Glucose concentrations were measured with a Yellow Springs Instruments (Yellow Springs, Ohio) Model 2000 glucose analyzer. Cells were harvested by centrifugation in a Sharpels (Philadelphia, Pa.) solid-bowl centrifuge.

When the cells (aerobically or anaerobically grown) had reached stationary phase (based on stable optical density measurements), they were harvested by centrifugation at 5000 g×30 min. Cell pellets were washed once with distilled water and recentrifuged (16,000 g×20 min). The washed cells were lyophilized and stored at −20° C. until used. Lyophilized cells (200 mg) were homogenized in chloroform/methonol/water (8/16/4.8 ml) with a Polytron Homogenizer (Brinkmann, Westbury, N.Y.), and lipids were extracted according to the method of Bligh and Dyer (1959. *Can. J. Biochem. Physiol.* vol. 37, pp. 911–916, herein incorporated by reference), where additional solvent (chloroform/water, 8/8 ml) was added to separate the mixture into two phases. The mixture was then centrifuged, and the lower lipid-containing phase was removed and retained.

In an alternative method for the extraction of THBH, lyophilized cells were extracted using 50 ml of chloroform/methanol (96/4, v/v) as solvent for each gram of cells. The mixture was shaken for at least one hour, and cellular debris was removed by vacuum filtration through a Whatman (Maidstone, England) glass microfiber filter (GF/A) with a pore size of 1.6 μm.

Purification of the hopanoids may be carried out by any method known in the art to be effective for the isolation of lipids. Suitable methods include chromatographic techniques, such as solid phase extraction, liquid chromatography, column chromatography and high performance liquid chromatography (HPLC), and all have been found to be effective (Roth et al., supra).

Initial screening was carried out on three hopanoids isolated from Z. mobilis (FIGS. 1,b,c,d). These compounds were purified as described and screened for their ability to inhibit three enzymes known for their activity in the metabolism of arachidonic acid. These enzymes, soybean 15-lipoxygenase (15-LO), human 5-lipoxygenase (5-LO) and prostaglandin H synthase (Table I), are known to be inhibited by most non-steroidal anti-inflammatory drugs (Parthasarathy and Rankin. 1992. Prog. Lipid. Res. vol. 31, p. 127). Soybean 15-LO was inhibited by one of the hopanoids, tetrahydroxybacteriohopane (THBH), with an $IC_{50}$ of about 10 μM. Chemical per-O-acetylation of THBH (THBH-Acet) destroyed its ability to inhibit this 15-LO. The two other natural hopanoid compounds, THBH-GA and THBH-Et, were also evaluated for their effect on soybean 15-LO. Not only did these compounds not inhibit soybean 15-LO, but they actually stimulated enzyme activity.

TABLE I

Effect of Tetrahydroxybacteriohopane (THBH), THBH-Acet, THBH-GA, THBH-Et and Known Inhibitors on Arachidonic Acid Metabolizing Enzymes.

| Enzyme | Inhibitor | Concentration (μM) | Enzyme Activity (Relative ± S.D.) |
|---|---|---|---|
| Soybean 15-LO | None | — | 100[a] |
| | THBH[b] | 6.75 | 68 ± 5 |
| | | 12.5 | 48 ± 9 |
| | | 25 | 15 ± 6 |
| | | 50 | 4 ± 3 |
| | | 100 | 11 ± 2 |
| | THBH-Acet | 25 | 89 ± 11 |
| | | 50 | 114 ± 17 |
| | THBH-GA | 25 | 172 ± 24 |
| | | 50 | 188 ± 14 |
| | THBH-Et | 25 | 151 ± 10 |
| | | 50 | 250 ± 38 |
| | Phenidone | 25 | 34 ± 4 |
| Human 5-LO | None | — | 100[c] |
| | THBH | 25 | 98 ± 2 |
| | | 50 | 97 ± 1 |
| | Phenidone | 25 | 55 ± 2 |
| Prostaglandin H Synthase | None | — | 100[d] |
| | THBH | 25 | 102 ± 3 |
| | | 50 | 103 ± 2 |
| | Indomethacin | 2.4 | 7 ± 2 |

[a]Enzyme activity in the absence of inhibitor was 20.8 μmole $O^2$ consumed/min/mg protein.
[b]For abbreviations, see Brief Description of the Drawings.
[c]Enzyme activity in the absence of inhibitor was 0.387 μmole $O^2$ consumed/min/mg protein.
[d]Enzyme activity in the absence of inhibitor was 2.78 μmole $O^2$ consumed/min/mg protein.

The two other arachidonic-acid metabolizing enzymes, human 5-LO and prostaglandin H synthase, were not significantly inhibited by 25 or 50 μM THBH. Because of the lack of inhibition of these enzymes by THBH, THBH-Acet, THBH-GA and THBH-Et were not evaluated for their effect on these two enzymes.

Because nonsteroidal anti-inflammatory drugs inhibit 5-LO, 15-LO and prostaglandin H synthase (Parthasarathy, supra), the finding that THBH selectively inhibits 15-LO without inhibiting either 5-LO or prostaglandin H synthase, suggested that THBH might have unique pharmacological properties. Since 15-LO is involved in atherosclerosis and asthma, the inhibitory data presented the possibility that THBH could be exploited for the treatment of these conditions. Further studies were thus carried out to evaluate anti-inflammatory capability of the compound.

The anti-inflammatory studies were carried out utilizing a topical model with arachidonic acid as the inflammation-inducing compound. 15-LO initiates the metabolic pathway leading to the formation of the lipoxins by converting arachidonic acid to 14-hydroperoxyeicosatetraenoic acid (15-HPETE). Lipoxins may share some of the bioactivity associated with leukotrienes, the end-product associated with the 5-LO arachidonic acid metabolic pathway. A solution of arachidonic acid was applied to the surface of a mouse ear with the test substance (THBH) applied 30 minutes later. Ear swelling was measured after an additional 60 minutes as an index of inflammation. For all test procedures, % inhibition was calculated according to the formula $$Ic-It/Ic \times 100 \qquad (1)$$

where Ic is the increase in ear thickness (mm) in control mice and It is the increase in ear thickness in treated mice (see Example 5).

Results are shown in Table II, where it is seen that THBH significantly affects swelling caused by the application of arachidonic acid.

Any hopanoid compound which effectively inhibits 15-LO activity is considered useful as an anti-inflammatory agent, and the inhibitory effect can easily be determined by following the testing procedure presented. A composition is prepared by mixing at least one hopanoid compound with a pharmaceutically acceptable carrier, the selection of which depends on the route of administration. Routes of administration include topical application, oral administration in liquid or solid form, injection and inhalation. Typical carriers may include alcohols, such as ethanol, and fatty acids such as oleic acid. Topical application would be in the form of ointments or salves. Inhalation may also require the inclusion of an acceptable propellant. In addition, other appropriate adjuvants such as surfactants and emulsifiers may also be included in the composition. The compounds may be used for the treatment of conditions such as asthma, atherosclerosis and skin inflammations. Dosages are formulated depending on the type and severity of condition being treated as well as on the route of administration, and the determination of these variables are within the level of skill in the art.

TABLE II

Topical Anti-Inflammatory Test Using BHTH Against Arachidonic Acid-Induced Inflammation.

| Compound | Route | Dose (mg/ear) | Swelling Ear Thickness Measurement[a] | | | % Inhibition |
|---|---|---|---|---|---|---|
| | | | Left Ear (No A.A.) | Right Ear (1 hr. A.A.) | Swelling (R - L) | |
| Control[b] | Topical | [c]100 μl/ear | 20.8 ± 0.2 | 37.2 ± 0.9 | 16.4 ± 0.9 | |
| BHTH | Topical | 10 | 22.0 ± 0.7 | 31.6 ± 1.5 | 9.6 ± 1.1 | 41 |
| Indo-methacin | Topical | 3 | 22.2 ± 0.5 | 29.4 ± 1.5 | 7.2 ± 1.5 | 56 |

Mice: ICR(♂) 25 ± 2 grams, n = 5/group
[a]($\bar{x}$ ± SEM) × 0.01 mm.
[b]Control = Acetone; DMSO was not suitable to use in the A.A. - induced topical anti-inflammatory test because DMSO will cause skin irritation and inflammation, necessitating the use of acetone as an alternative solvent.
[c]Because of poor solubility of BHTH in acetone, a larger volume of 100 μl acetone was used to dissolve 10 of sample to apply to animal ear entirely.

The following examples a re intended only to further illustrate t h e invention and are not intended to limit the scope of the invention as defined by the claims.

EXAMPLES

Example 1
Purification of Bacterial Hopanoids.

The bacterium Z. mobilis was grown anaerobically in a 40-liter fermentor and harvested by centrifugation. Lyophilized cells were extracted by chloroform-methanol, and the three major hopanoids were purified using sold phase extraction and semi-preparative HPLC methods.

Solid phase extraction was carried out by column chromatography using amino-propyl solid-phase extraction cartridges (IST Isolute, Lakewood, Colo., and Varian BondElut, Sunnyvale, Calif.) in order to separate THBH from the remaining hopanoids in the sample. Three sizes of columns were used, containing 500 mg, 5 g and 10 g of sorbent, respectively. A gram of sorbent holds approximately 0.7 ml of solvent. The column was conditioned by washing first with 7 bed vol of methanol followed by 14 bed vol of chloroform/methanol (96/4, v/v). (Column conditioning is not essential and may be eliminated.) Lipids were extracted by homogenizing 200 mg of lyophilized cells with chloroform/methoanol/water (8/16/4.8 ml), followed by adding additional solvent (chloroform/water, 8/8 ml) to separate the mixture into two phases. The mixture was centrifuged, and the lower phase containing lipids was removed (Bligh and Dyer. 1959. Can. J. Biochem. Physiol. vol. 37, pp. 911–917) and redissolved in chloroform/methanol (96/4, v/v) at a concentration of 2 mg/ml and applied to the column. [Note: When lyophilized cells were extracted with chloroform/methanol (96/4, v/v), the entire filtrate was put directly onto the column, eliminating the need to evaporate the solvent from the lipid extract and to redissolve the lipid in chloroform/methanol (96/4, v/v).] The column was washed with 7 bed vol of chloroform/methanol (96/4, v/v) to remove the nonpolar lipids and fatty acids. The hopanoids were eluted immediately afterwards using 20 bed vol of acetone followed by 7 bed vol, 3 bed vol, and 3 bed vol of acetone.

The semipreparative HPLC method used to separate a mixture of the hopanoids THBH-GA and THBH-Et utilized a LiChrosorb Si-60 column, 10×250 mm (Alltech, Deerfield, Ill.). The mobile phase was hexane/isopropanol/0.04% triethylamine in water (40/54/6, v/v/v), and the flow rate was 5 ml/min. Output from the column was monitored by connecting the effluent to a fixed splitter where 10% of the flow was diverted into a flame ionization detector (Tremetrics Model 945, Austin, Tex.) and the remaining 90% was available for manual fraction collection. The detector was capable of evaporating this solvent flow rate (0.5 ml/min) with very low background noise.

THBH was per-O-acetylated by removing the solvent and shaking about 1 mg of sample with a mixture of 1 ml acetic anhydride and 1 ml pyridine, at room temperature for 18 hr. Acetic anhydride and pyridine were removed via a stream of nitrogen.

Example 2
Assay of Soybean 15-Lipoxygenase.

Soybean 15 LO (Type V) was obtained from Sigma Chemical Co. (St. Louis, Mo.). The reaction mixture (1.8 ml) consisted of 0.1 M borate buffer, pH 9.0, 5 μl (0.5 μg, 315 units) of soybean 15-LO dissolved in borate buffer, and 25 μl of inhibitor dissolved in ethanol, and was preincubated for 3 min. The reaction was started by injecting 100 μl of substrate mixture (prepared fresh daily and consisting of 1.0 mg arachidonic acid sonicated in 2.3 ml 0.1 M borate buffer, pH 9.0) yielding a final concentration of 50.9 μM arachidonic acid in the reaction vessel. The rate of disappearance of dissolved oxygen was monitored with a Clark Oxygen Electrode (Yellow Springs Instruments, Yellow Springs, Ohio) with the temperature controlled at 25° C., according to the method described by Breton et al. (1993. Prostaalandins, Leucotrienes, and Fatty Acids. vol. 49, p. 929, herein incorporated by reference). The $O_2$ concentration in an air-saturated aqueous solution at 25° C., was calculated to be 0.24 mM. The assay system was checked by measuring the inhibition of phenidone, a known inhibitor of soybean 15-LO. Each potential inhibitor was tested at each of the listed concentrations at least three times and enzyme activities presented are the means ± standard deviations, reported as relative activities (calculated assuming that the activity in the minus-inhibitor control=100). The actual activities of the controls (in units of μM $O_2$ consumed/min/mg protein) are also presented as a footnote to Table I.

Example 3
Assay of Recombinant Human 5-Lipoxygenase.

Recombinant human 5-LO was obtained from Oxford Biomedical Research Co., Oxford, Mich. The reaction mixture (1.80 ml) consisted of 0.25 mM $CaCl_2$, 0.13 mM ATP, 7 μl of phosphatidylcholine (12 μg/2 ml ethanol), 25 μl of inhibitor dissolved in ethanol, and Tris-HCl buffer, 50 mM, pH 7.4, and preincubated for 3 min. The reaction was started by injecting 5 µl of arachidonic acid (3.8 mg/5 ml ethanol) yielding a final arachidonic acid concentration of 4.5 µM in the reaction mixture. The rate of disappearance of dissolved oxygen was monitored with an oxygen electrode at 37° C., as described in Example 2. The $O_2$ concentration in an air-saturated aqueous solution at 37° C. was calculated to be 0.185 mM. The assay system was checked by measuring the inhibition of phenidone, a known inhibitor of human 5-LO.

Example 4
Prostaglandin H Synthase (Cyclooxygenase).

Prostaglandin H synthase was obtained from Oxford Biomedical Research Co., Oxford, Mich. The reaction mixture (1.80 ml) consisted of 0.5 mM phenol, 1 µM hematin, enzyme (3.75 µg in 5 µl), 25 µl of inhibitor dissolved in ethanol, and potassium phosphate buffer (0.1 M, pH 7.8), and was preincubated for 3 min. The reaction was started by injecting 15 µl of arachidonic acid dissolved in ethanol, yielding a final concentration of 100 µM arachidonic acid in the reaction vessel. The disappearance of dissolved oxygen was monitored as described in Example 2. The assay system was checked by measuring the inhibition in indomethacin, a known inhibitor of prostaglandin H synthase.

Example 5
Anti-Inflammatory Topical Test.

Arachidonic acid (2 mg in 20 µl acetone:pyridine:water) in a ratio of 7:2:1) was applied topically to the anterior and posterior surfaces of the right ear of mice 30 min following similar application of hopanoid or control (20 µl). Swelling of the ear was then measured by a Dyer model micrometer gauge after 60 min as an index of inflammation. For all test procedures, % inhibition was calculated according to formula (1). Five mice/dose level of test substance were used with negative and positive control groups run concurrently. The positive control was indomethacin.

We claim:

1. A composition comprising at least one hopanoid effective as an anti-inflammatory agent, and an acceptable pharmaceutical carrier.

2. The composition of claim 1, wherein said at least one hopanoid blocks 15-lipoxygenase activity and lipoxin biosynthesis.

3. The composition of claim 1, wherein said at least one hopanoid is tetrahydroxybacteriohopane.

4. The composition of claim 1, wherein said acceptable pharmaceutical carrier is an alcohol, a fatty acid, a salve or an ointment.

5. The composition of claim 1, wherein said composition additionally comprises an adjuvant, and wherein said adjuvant is a surfactant or an emulsifier.

6. The composition of claim 1, wherein said composition additionally comprises a propellant.

7. The composition of claim 5, wherein said composition additionally comprises a propellant.

* * * * *